(12) United States Patent
Small et al.

(10) Patent No.: US 6,551,791 B1
(45) Date of Patent: Apr. 22, 2003

(54) RAPID DIAGNOSTIC METHOD FOR DISTINGUISHING ALLERGIES AND INFECTIONS AND NASAL SECRETION COLLECTION UNIT

(75) Inventors: Parker Small, Gainesville, FL (US); Shih-Wen Huang, Gainesville, FL (US); Ronald Kudla, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/597,360

(22) Filed: Jun. 19, 2000

Related U.S. Application Data

(63) Continuation-in-part of application No. PCT/US99/05751, filed on Mar. 16, 1999, which is a continuation-in-part of application No. 08/621,557, filed on Mar. 25, 1996, now Pat. No. 5,910,421, which is a continuation-in-part of application No. 08/576,604, filed on Dec. 21, 1995, now abandoned.

(51) Int. Cl.$^7$ .................................................. C12Q 1/44
(52) U.S. Cl. ............................ 435/19; 435/34; 436/811
(58) Field of Search ...................... 435/19, 34; 436/811

(56) References Cited

U.S. PATENT DOCUMENTS

| | | | |
|---|---|---|---|
| 4,968,633 A | | 11/1990 | Marcucci |
| 5,200,321 A | | 4/1993 | Kidwell |
| 5,369,007 A | | 11/1994 | Kidwell |
| 5,643,202 A | | 7/1997 | Gravenstein et al. |
| 5,910,421 A | * | 6/1999 | Small et al. ................. 435/19 |

FOREIGN PATENT DOCUMENTS

| | | |
|---|---|---|
| FR | 2784023 A | 4/2000 |
| WO | WO 0055359 A | 9/2000 |

OTHER PUBLICATIONS

Lans, D.M. et al., "Nasal Eosinophilia in Allergic and Nonalergic Rhinitis: Usefulness of the Nasal Smear in the Diagnosis of Allergic Rhinitis", Allergy Proceedings, Jul. 4, 1989, vol. 10 No. 4 pp. 275–280, , Ocean Side Publications, USA.

Naclerio, R.M. et. al., "Mediator Release After Nasal Airway Challenge with Allergen 1–4", American Review of Respiratory Diseases, Oct. 4, 1983, vol. 28, No. 4 pp. 597–602, USA.

* cited by examiner

*Primary Examiner*—Ralph Gitomer
(74) *Attorney, Agent, or Firm*—Van Dyke & Associates, P.A.

(57) ABSTRACT

A method and device for rapidly, non-invasively and inexpensively differentiating between allergic rhinitis, upper respiratory tract viral infection and bacterial sinusitis, comprising a support strip upon which is fixed discrete indicators of pH, protein content, nitrite content, leukocyte esterase activity, and eosinophil content or other measure of a substance found in allergic secretions, such as TAME esterase, of a sample with which said reagent test strip is contacted. Contact of a nasal secretion with the device of this invention permits differentiation between allergic, bacterial and viral conditions, based on pH, protein content, leukocyte esterase activity, nitrite content, eosinophil content and TAME esterase activity. The invention further provides a novel means for collecting nasal secretions to facilitate differential diagnosis of sinusitis, upper respiratory tract viral infection and allergic rhinitis.

8 Claims, 3 Drawing Sheets

Sinusitis

RAPID DIAGNOSTIC METHOD FOR DISTINGUISHING ALLERGIES AND INFECTIONS AND NASAL SECRETION COLLECTION UNIT

CROSS REFERENCES TO RELATED APPLICATIONS

This application is a continuation-in-part of PCT application serial number PCT/US99/05751, filed Mar. 16,1999, which in turn was a continuation-in-part of application Ser. No. 08/621,557, filed Mar. 25, 1996, now U.S. Pat. No. 5,910,421, which was a continuation in part of application Ser. No. 08/576,604, filed on Dec. 21, 1995, now abandoned.

BACKGROUND OF THE INVENTION

I. Field of the Invention

This invention is a rapid and simple method for the differential diagnosis of allergies, sinusitis and upper respiratory tract infections. The method involves the use of either commercially available or novel, specifically adapted, indicator or reagent test strips which are contacted with nasal secretions. Based on the differential read-out from the indicator strip, and a measure of eosinophil infiltration or other substance in the nasal secretion, a user of the strip is able to determine, with the assistance of a scoring method disclosed herein, whether an allergic condition, a viral infection or bacterial sinusitis is the cause of the respiratory discomfort. In particular, this invention provides an improved device for providing differential diagnosis whereby a patient may easily deposit nasal secretions on the indicator elements by blowing their nose into a container, such as a bag, in which the indicator device may be inserted, or in which the indicator element forms an integral part.

II. Background

It is common for patients afflicted with respiratory discomfort to seek the advice of a clinician in an effort to minimize or overcome their discomfort. Such discomfort generally is attributable to one of the following etiologies: allergic reactions, viral upper respiratory tract infections (URIs), or bacterial infections which can produce sinusitis. However, the clinician presented with such a patient typically has the daunting task of determining which of these three principal etiologies is responsible for the discomfort experienced by a particular patient. The danger inherent in a mis-diagnosis can be quite severe. For example, should the clinician incorrectly diagnose an allergy as sinusitis, a course of antibiotics would typically be prescribed. Naturally, such treatment would do little to alleviate the allergic discomfort being experienced by the patient while at the same time, the patient is exposed to an antibiotic to which there is a possibility of raising a resistant bacterial infection. Should this occur, a problem much more severe than the original allergic condition will have been unwittingly engendered. The prevalence of antibiotic-resistant strains on a global scale due to the over-prescribing of antibiotics has become an increasingly recognized problem (Service, R. F., 1995).

In the foregoing example, the availability of a rapid and simple differential diagnostic method would, instead of resulting in a compounded problem, result in the simple recommendation by the clinician that the patient adhere to a course of antihistamine treatment, allergen avoidance, and/or a regimen of toleragenic desensitization. Unfortunately, however, to date, there is no such simple procedure which will provide the clinician with the necessary differential diagnosis. An accepted method of diagnosis for bacterial sinusitis is expensive radiologic imaging (typically X-ray or CT-scan) of the patients' sinuses (see Katz et al., 1995).

Many scientific articles have appeared addressing one or another of the various etiologies of respiratory discomfort. However, no rapid, inexpensive differential diagnostic method has been found. Thus, for example, Wang et al., *Correlations between Complaints, Inflammatory Cells and Mediator Concentrations in Nasal Secretions after Nasal Allergen Challenge and during Natural Allergen Exposure*, Int. Arch. Allergy Immunology 1995; 106:278–285, disclosed a method of using a nasal microsuction technique. They showed that nasal allergen challenge (NAC) of asymptomatic (out of season) seasonal allergic rhinitis patients results in immediate (5 minutes) increases in histamine, leukotriene C4 (LTC4), and tryptase, with a more gradual (one hour post NAC) and prolonged increase in eosinophil and eosinophil cationic protein (ECP) concentration in nasal secretions. By contrast, in symptomatic (in season allergic rhinitis) patients, high concentrations of eosinophils, ECP, LTC4 and histamine, but not tryptase, were observed. It was concluded that allergic rhinitis is a chronic inflammation of the nasal mucosa, and that infiltration of eosinophils and release of late-phase inflammatory mediators are the predominant pathophysiologic markers. However, this publication neither teaches nor suggests that these observations can be applied to distinguish patients suffering from an allergic condition as opposed to an infection. In addition, the methods used by these authors are laborious and time-consuming and do not involve the use of reagent test strips. Sigurs et al., *Eosinophil cationic protein in nasal secretion and in serum and myeloperoxidase in serum in respiratory syncytial virus bronchiolitis: relation to asthma and atopy*, Acta Paediatr 1994; 83:1151–5, concluded that it is not possible to predict, from eosinophil cationic protein/albumin ratios in nasal secretions or from ECP and myeloperoxidase concentrations in serum, whether children with respiratory syncytial virus (RSV) bronchiolitis would develop asthma. The publication provides no teaching or suggestion of a method which can easily distinguish patients suffering from an allergic condition as opposed to an infection. The methods used by these authors are laborious and time-consuming and do not involve the use of reagent test strips. Okuda et al., *A Novel Method of Counting Eosinophils in Nasal Secretion of Allergic Rhinitis by Hemocytometric Method*, Int. Arch. Allergy Immunol. 1994; 104 (suppl. 1):6, disclosed a rapid method for quantifying the number of eosinophils in nasal secretions as a method for diagnosis of allergic rhinitis. The method involves preparation of a solubilized sample of nasal secretion and counting of whole eosinophils. There is no mention of reagent test strips and there is no mention of a method for distinguishing patients suffering from an allergic condition as opposed to an infection.

Kowalski et al., *Neutrophil chemotactic activity (NCA) in nasal secretions from atopic and non-atopic subjects*, Allergy 1993; 48:409–414, reported that basal nasal secretions of both healthy persons and patients with chronic rhinitis contain significant chemotactic activity to neutrophils. The study also reports that there is an increase in protein content of nasal secretions in patients with perennial allergic rhinitis (AR) following challenge with an antigen. There is no mention of reagent test strips and there is no mention of a method for distinguishing patients suffering from an allergic condition as opposed to an infection.

Igarashi et al, *Analysis of nasal secretions during experimental rhinovirus upper respiratory infections*, J. Allergy Clin. Immunol. 1993; 92:722–731, studied patients with allergic rhinitis or control subjects inoculated with rhinovirus. Nasal lavage samples pre-and post-infection were analyzed for protein and mast cell mediators. It was found that total protein (including the plasma proteins albumin and IgG and the glandular proteins lactoferrin, lysozyme and secretory IgA) increased post-infection, predominantly due to increased vascular permeability. It was also found that the allergic subjects had fewer symptoms, but greater vascular permeability and greater histamine secretion than control subjects post-rhinovirus infection. Protein was determined by the bicinchoninic acid protein assay (Pierce Chemical Co.) on aliquots of nasal lavage. It is noted at several points in the publication that the symptoms of rhinovirus infected patients and patients with nasal allergic reactions are similar, thus teaching away from the possibility that a simple nasal secretion assay method could be used to distinguish these conditions. Inasmuch as this study is directed at determining the differences in nasal secretions between rhinovirus infected normal or allergic individuals, the study addresses a different problem than that addressed by the instant invention, which is a method for measuring the differences in nasal secretions of patients infected with a rhinovirus, for example, and a patient not infected with a rhinovirus but suffering from allergic rhinitis. The methods used by these authors are laborious and time-consuming and do not involve the use of reagent test strips.

Sperber et al., *In vivo detection of a novel macrophage-derived protein involved in the regulation of nasal mucus-like glycoconjugate secretion*, J. Allergy Clin. Immunol. 1993; 92:581–588, disclosed a study directed at characterization of a novel 68 Kd nasal mucus secretagogue (NMS-68) released by monocytes. Inasmuch as this protein was found to be present in nasal tissue of patients with allergic and non-allergic rhinitis, it does not appear to provide a method for distinguishing between these conditions, although the baseline level of this protein is more elevated in the allergic patients. Reagent test strips were not used in this study.

Knani et al., *Indirect evidence of nasal inflammation assessed by titration of inflammatory mediators and enumeration of cells in nasal secretions of patients with chronic rhinitis*, J. Allergy Clin. Immunol.1992; 90:880–889, examined the nasal lavage cells and six inflammatory mediators released in nasal secretions of four groups of patients with perennial rhinitis and a control group. It was found that patients with symptomatic allergic rhinitis had increased levels of eosinophils, as well as of eosinophil protein X (EPX), LTC4/D4, tryptase, MPO and PGD2. Patients with non-allergic rhinitis were found to have increased neutrophil, tryptase, MPO and EPX concentrations. These measurements provided indirect evidence of nasal inflammation. However, there was no analysis of differences between the nasal secretions of rhinitis patients and patients suffering, for example, from a rhinoviral infection or a bacterial sinus infection.

Klementsson et al., *Eosinophils, secretory responsiveness and glucocorticoid-induced effects on the nasal mucosa during a weak pollen season*, Clinical and Experimental Allergy 1991; 21:705–710, analyzed the eosinophil influx, the concentration of ECP and secretory responsiveness following methacholine challenge in nasal lavage samples of patients with allergic rhinitis. There was no concurrent analysis of nasal secretions from patients with bacterial sinus or viral infections, and reagent test strips were not employed.

Gordon et al., *The pathophysiology of rhinitis*, J. Allergy Clin. Immunol. 1991; 88:33–42, challenged patients with seasonal rhinitis on one side of the nose with an allergen and nasal secretions from both sides of the nose were analyzed for protein and mediators. There was no concurrent analysis of nasal secretions from patients with bacterial or viral infections, and reagent test strips were not employed.

Cohen, R. A, and Brestel, E. P., *Nasal secretory response to allergen provocation*, 1988; 18:435–443, analyzed nasal lavage samples from ragweed-sensitive and control subjects following ragweed pollen challenge. The study revealed no increase in total protein, albumin, potassium, lysozyme activity or peroxidase activity in the control subjects. There were increases in all of these constituents in the ragweed-sensitive subjects. These constituents were assayed by dye binding (Bradford), rocket immunoelectrophoresis, absorption spectroscopy, ABTS (Sigma Chemical Co.) oxidation, and radial diffusion, respectively. Use of reagent test strips is neither taught nor suggested, nor is there a concomitant analysis of these constituents in bacterially or viral infected, no-allergic subjects. Liu et al., *Injurious effect of eosinophil extract on the human nasal mucosa*, Rhinology 1988; 26:121–132, attempted to elucidate the role of eosinophils in nasal secretions of allergic subjects. These authors conclude that the eosinophil extracts tested may actually be harmful to the function of human nasal mucosa. Use of reagent test strips is neither taught nor suggested, nor is there a concomitant analysis of these constituents in infected subjects.

Anderson et al., *Allergen-induced nasal hyperactivity appears unrelated to the size of the nasal and dermal immediate allergic reaction*, Allergy 1987. 42:631–637, analyzed "priming", in which nasal lavage samples from hay fever patients were tested following an initial and a re-challenge with allergen. The biochemical parameter used as the measure of the allergic reaction was TAME-esterase via a radiochemical method (release of tritium labeled methanol from the synthetic substrate H3-TAME). Use of reagent test strips is neither taught nor suggested, nor is there a concomitant analysis of these constituents in infected subjects.

Settipane, G. A, and Klein, D. E., *Non Allergic Rhinitis: Demography of Eosinophils in Nasal Smear, Blood Total Eosinophil Counts and IgE Levels*, NER Allergy Proc.1985; 6:363–366, in an attempt to develop a methodology for differential diagnosis of patients with non-allergic rhinitis, evaluated patients with rhinitis and negative skin tests, (taken to mean that their rhinitis had a non-allergic etiology), for cause of the rhinitis. Nasal smears from these patients were obtained by rolling a swab with nasal secretions on a glass slide, fixing with methanol, staining with Camaco stain (Wright-Giemsa stain), and counting the number of eosinophils per 100 cells. Sinus X-rays were conducted to detect sinusitis. NARES, non-allergic rhinitis with eosinophilia syndrome, is clinically defined in the paper as "nasal congestion/rhinorrhea with negative allergy skin tests, normal serum IgE, and >5% eosinophils in the nasal smear." The purpose of the study was "to attempt to corroborate NARES as a new syndrome and to attempt to further classify and clarify non-allergic rhinitis." There was no discussion in this paper regarding the problem of mis-identification of this clinical condition with upper respiratory tract infections, and use of reagent test strips as part of the differential diagnosis is neither disclosed nor suggested.

Brofeldt, et al., *Biochemical Analysis of Nasal Secretions induced by Methacholine, Histamine, and Allergen Provocations*, Am. Rev. Respir. Dis. 1986; 133:1138–1142, obtained methacholine, histamine and allergen induced nasal secretions from subjects over a fifteen minute post-induction period. The nasal secretions were weighed and tested for hexose content (orcinol method), protein content (Lowry method), carbohydrate (gas liquid chromatography), sialic acid (calorimetric thiobarbituric acid assay), inorganic sulphate (radioactive BaCl2), DNA (diphenylamine), albumin and immunoglobulins (rocket immunoelectrophoresis or ELISA). The different inducers were found to have differential effects on the various elements tested. However, there was no concomitant study of nasal secretions from patients suffering from an infection nor was the use of reagent test strips taught or suggested.

Eggelston, et al., *Mediators of Immediate Hypersensitivity in Nasal Secretions during Natural Colds and Rhinovirus Infection* Acta Otolaryngol. 1984; suppl. 413:25–35, note that "[v]iral respiratory infections and allergic rhinitis have many similarities. Not only are symptoms similar in the two conditions, but the pathologic anatomy of both is dominated by vascular dilatation and edema with minimal cellular infiltrate in acute phases . . . " The authors postulated that these similarities are due to mast cell activation during infection, resulting in release of histamine. However, they report that spectrofluorometric analysis of histamine in nasal secretions of control subjects or patients with a natural cold or with a rhinovirus infection does not support this hypothesis. Histamine concentrations were found to be generally lower in individuals infected with influenza A or rhinovirus. TAME-esterase was also found not to be elevated during these infections. This article reports that during viral respiratory tract infection there is little or no TAME-esterase elevation, while in allergic rhinitis there is TAME esterase elevation (see discussion at page 34 of the reference). However, the use of reagent test strips for this purpose is neither taught nor suggested, nor is there a discussion of how these results could be used in a differential diagnostic method also aimed at distinguishing sinusitis.

Baumgarten, et al, *Plasma Kallikrein During Experimentally Induced Allergic Rhinitis: Role in Kinin Formation and Contribution to TAME-Esterase Activity in Nasal Secretions,* J. Immunol. 1986; 137:977–982, report the observation that when allergic and non-allergic individuals are challenged intranasally with an allergen, post-challenge nasal lavages of only the allergic individuals contained elevated levels of immunoreactive human plasma kallikrein/prekallikrein (iHPK). This increase in iHPK correlated with increases in kinins, histamine, TAME-esterase, and clinical symptoms. In fact, these researchers argue that the TAME-esterase activity is produced by plasma kallikrein and mast cell tryptase. Thus, iHPK may be an additional marker that could be used in a reagent test strip for allergic rhinitis diagnosis. However, in this study, esterase was assayed by a radiochemical method and kinins were assayed using a radioimmunoassay, rather than by any type of reagent test strip.

Anderson et al., *Mechanisms of nasal hyper-reactivity,* Eur. Arch. Otorhinolaryngol. 1995; 252 (suppl. 1):S22–S26, review the factors known to be involved in allergen-induced nasal hyper-reactivity. However, there is no teaching or suggestion of a method for distinguishing allergic from infection related rhinitis. Reagent test strips for this purpose are neither proposed nor suggested.

Florman, et al., *Rapid Non-invasive Techniques for Determining Etiology of Bronchitis and Pneumonia in Infants and Children,* Clin. Chest Med. 1987; 8:669–679, provide a review of techniques for differential diagnosis of the causative agent in lower respiratory tract infections. A number of rapid, non-specific and specific tests are mentioned. However, there is no mention of differential diagnosis of allergic from infective conditions and reagent test strips for this purpose are neither disclosed nor suggested.

Katz et al., *A comparison of Imaging Techniques in Patients with Chronic Sinusitis* (X-Ray, MRI, A-Mode Ultrasound) *Allergy Proc.* 1995. 16:123–127, demonstrate the long-felt need for a rapid, inexpensive way to diagnose sinusitis and distinguish this condition from allergic rhinitis. The method of the instant invention has the potential for supplanting the much more expensive diagnostic techniques reported in this paper to be most reliable in diagnosis of sinusitis (CAT scans and MRI).

Demoly et al., *Assessment of Inflammation in noninfectious chronic maxillary sinusitis,* J. Allergy Clin. Immunol. 1994; 94:95–108, suggest that it might be possible to distinguish sinusitis (infection) from allergic rhinitis based on the contents of nasal mucosa. However, the techniques used in attempting to distinguish these conditions depended on the use of immunohistochemistry of surgical specimens, immunocytochemistry of lavage fluids, and measurement of specific inflammatory mediators in sinus lavage fluids (ELISA, RIA). There is no teaching or suggestion that reagent dip-sticks could be used for this purpose.

Accordingly, there has been a long-felt need in the art for a rapid, inexpensive, non-invasive technique for a method capable of distinguishing between allergies and infections. The method of the instant invention involves testing nasal secretions with commercially available (Ames Division, Miles Laboratories, Inc., Elkhart, Ind. 46515, or Boehringer Mannheim Corporation, Advanced Diagnostics, 9115 Hague Road, P.O. Box 50457, Indianapolis, Ind. 46250–0457) or novel or modified reagent test strips. The commercially available strips, also referred to as dipsticks, test for pH, protein, glucose, ketone, white blood cell esterase, bilirubin and blood.

The following U.S. Patents which may be relevant to the instant invention are listed on the product insert of the Miles Laboratories Inc., reagent test strips, and are herein incorporated by reference:

1) U.S. Pat. No. 3,438,737—Protein test composition and method of detecting proteins in fluids using the test composition.
2) U.S. Pat No. 4,301,115—Test device having resistance to cross contamination between reactant areas and process for making it.
3) U.S. Pat. No. 4,637,979—Composition and test device for determining the presence of leukocytes containing a zwitterion coupling agent for determining the presence of leukocytes, esterase or protease in a sample.
4) U.S. Pat. No. 4,645,842—Pyrrole composition for detecting presence of hydrolytic analytes, useful in the detection of leukocytes, esterase and protease in a test sample.
5) U.S. Pat. No. 4,657,855—Composition and test device for determining the presence of leukocytes, esterase and protease in a test sample.
6) U.S. Pat. No. 4,704,460—Novel compounds for detecting the presence of hydrolytic analytes in a test sample which indicates the presence of leukocytes, esterase and protease in a test sample.
7) U.S. Pat. No. 4,758,508—Analytical process and agents for the detection of esterolytic and/or proteolytic enzymes in a liquid sample.

The following U.S. Patents which may be relevant to the instant invention are listed on the product insert or packaging of Boehringer Mannheim Corporation's reagent test strips, and are herein incorporated by reference:

1) U.S. Pat. No. 3,359,072—A protein determination method.
2) U.S. Pat. No. 3,418,079—A protein determination device and method.

3) U.S. Pat. No. 3, 712,853—A nitrite detection reagent and method.
4) U.S. Pat. No. 3,897,214—A diagnostic device.
5) U.S. Pat. No. 3,802,842—A reagent test strip.
6) U.S. Pat. No. 4,013,416—A protein detection method.
7) U.S. Pat. No. 4,385,114—An oxidation indicator system.

However, none of these patents disclose or suggest a method for testing nasal mucous secretions to distinguish allergic from infectious conditions.

In the method of this invention, a sample of a patient's nasal secretions is tested and, based on the pH, amount of protein, nitrite and leukocyte esterase, it can quickly be determined if the patient is suffering from bacterial sinusitis. The secretions can also be tested for eosinophils, eosinophil components, TAME esterase, and if present in sufficient amounts, a diagnosis of allergy can be made. Viral infections can be deduced by the absence of allergy or sinusitis. The method has the potential to supplant much more expensive and invasive clinical procedures. In addition, the present invention provides an improvement to that which is disclosed in application Ser. No. 08/576,605, now U.S. Pat. No. 5,910,421, of which the present disclosure is a continuation-in-part. The improvement provided herein is a collection device for home or point of use care for the collection of nasal secretions and conducting diagnosis therewith without end user contact with the sample. That is, the present invention disclosure provides for a self-contained collection device. Features which may be incorporated into various embodiments of this device include air vents, foldable sealing means, patient identification means, and the like, as disclosed in further detail herein below.

BRIEF DESCRIPTION OF THE INVENTION

This invention provides a method for rapidly, non-invasively and inexpensively differentiating between allergic rhinitis and respiratory viral or bacterial infections. The method involves measuring, for example, by contacting a reagent test strip with a sample of nasal secretion, a series of agents in nasal secretions. The reagent test strip provides information on the pH, protein content, nitrite content, leukocyte esterase activity and preferably also provides information on the level of eosinophil infiltration in the sample contacted, such that a combination of a pH between about 7.5 and 9, a moderately strong presence of protein, at least a trace of leukocyte esterase and nitrite (see scoring system below) indicates the presence of a bacterial infection (sinusitis). The combination of a pH between about 5.0 and 7.5, little or no protein, little or no leukocyte esterase activity and little or no eosinophil infiltration or TAME esterase activity, is an indication of viral upper respiratory infection (URI). However, the same profile as in URI viral infection but with clear indication of eosinophil infiltration, TAME esterase activity or both is an indication of allergic rhinitis. As noted above, Eggelston et al., and Baumgarten et al., have noted that TAME-esterase is not elevated during influenza A or rhinoviral infections, while in allergic rhinitis, there is esterase elevation. Accordingly, in one embodiment of the present invention, a chromogenic substrate, such as Tosyl-Arg-paranitrophenol ester or paranitroaniline, Z-Arg-paranitroaniline (Bachem, Cat. #L1220), a derivative of Tosyl-Arg-paranitro phenol ester designed to liberate 3-hydroxy-5-phenyl pyrrole, which may then be reacted with a diazonium salt, B-z-Arg-paranitroaniline, or like colorimetric reagents or TAME-like substances or substrates, are included as diagnostic discriminators for allergic rhinitis. Development of color on contact of this reagent with nasal secretion therefore would be indicative of allergic rhinitis.

Also provided is a reagent test strip specifically adapted for rapidly, non-invasively and inexpensively differentiating between allergy and respiratory infection. The reagent test strip is adapted to provide information on the pH, protein content, nitrite content, leukocyte esterase activity, eosinophil infiltration and TAME esterase activity of the sample contacted, such that the method of this invention can quickly and easily be practiced.

In addition, this invention provides a practical, simple and safe collection device for collection of nasal secretions. The collection device may contain integral indicators for providing the differential diagnosis, or the collection device may be adapted such that a separate indicator device may be used to provide the differential diagnosis based on the nasal secretions collected therein.

Figure 1:
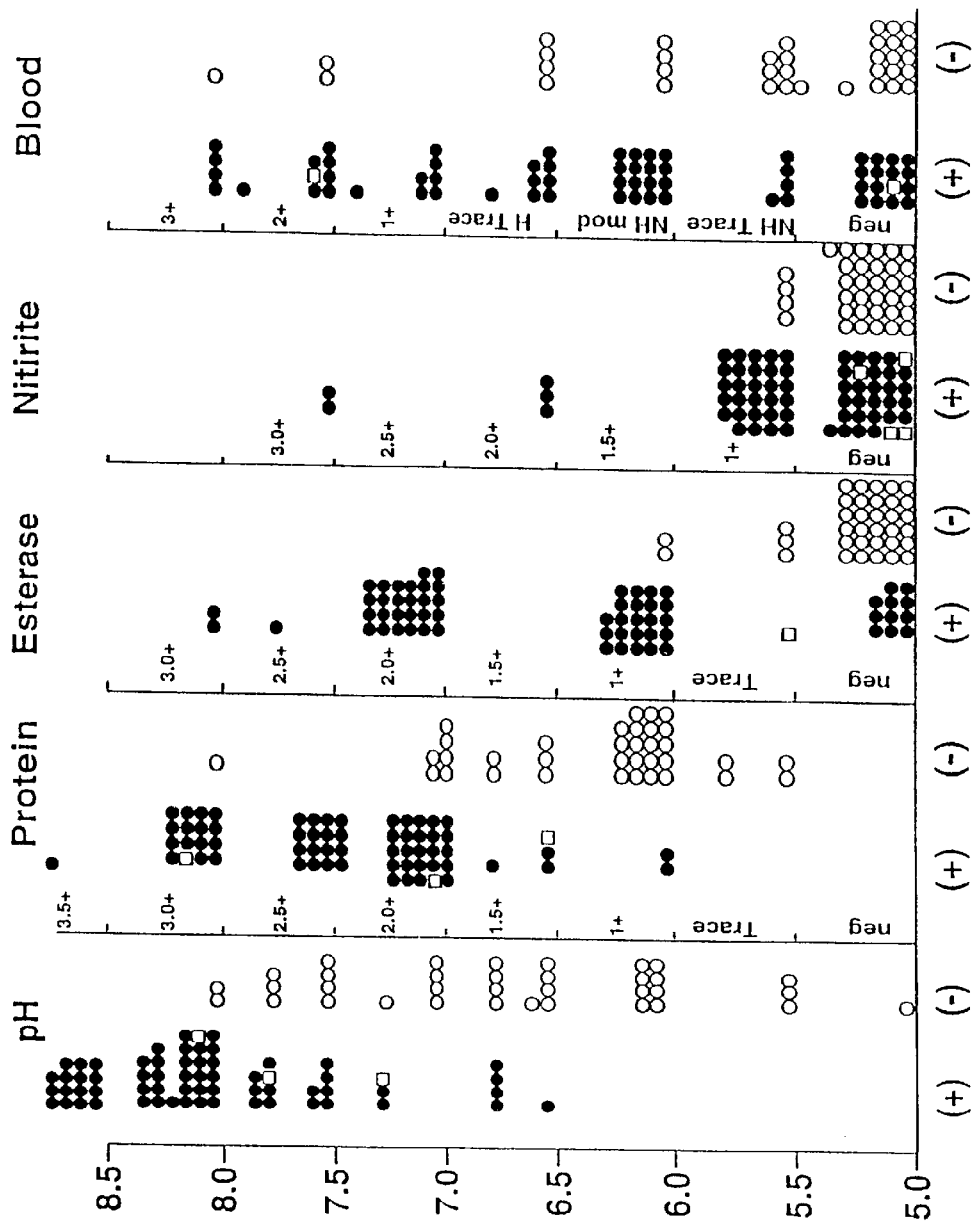
FIG. 1 shows the different chemical read-outs obtained by contacting reagent test strips with the nasal secretions of multiple patients presenting with respiratory discomfort. Closed circles (●) represent patients with radiologically proven sinusitis; open circles (○) represent patients having no sinusitis based on radiological investigation; open squares (□) represent patients with radiologically proven sinusitis that were at least partially treated with antibiotics prior to or during the evaluation period.

Accordingly, it is an object of this invention to provide a safe, simple and self-contained device for providing differential diagnosis between sinusitis, viral respiratory tract infection, and allergic rhinitis.

A further object of this invention is to provide a novel nasal secretion collection device.

DETAILED DESCRIPTION OF THE INVENTION

This invention is a method for non-invasively, rapidly and simply distinguishing between allergies and infections which involves testing nasal secretions for the levels of a number of agents. Preferably the method comprises contacting nasal secretions with commercially available (for example, from Ames Division, Miles Laboratories, Inc., Elkhart, Ind. 46515, or from Boehringer Mannheim Corporation, Advanced Diagnostics, 9115 Hague Road, P.O. Box 50457, Indianapolis, Ind. 46250–0457) or novel specifically adapted reagent test strips. The commercially available strips, also referred to as dipsticks, typically test for pH, protein, nitrite glucose, ketone, white blood cell esterase, bilirubin and blood.

In the method of this invention, a sample of a patient's nasal secretions is contacted with a reagent test-strip and, based on the pH, presence or absence of protein, levels of nitrite, leukocyte esterase and a measure of eosinophil infiltration in the nasal secretion, it can quickly be determined if the patient is suffering from an allergic reaction, a viral infection or a bacterial sinusitis infection. The method has the potential to supplant much more expensive and invasive clinical procedures. In the method of this invention, a commercially available reagent test-strip, or a novel, specifically adapted reagent test-strip, is contacted with a sample of a patient's nasal secretions. The patient may be any mammal, including an animal or a human. Based on the differential read-out from the reagent test-strip, which preferably includes a measure of eosinophil infiltration, TAME esterase activity or both, a determination can be made as to whether an allergy, sinusitis or a viral infection is responsible for upper-respiratory tract discomfort. With respect to commercially available reagent test-strips, those sold by the Ames Division of Miles Laboratories or the Boehringer Mannheim Corporation are generally acceptable. These test-strips may be made as disclosed herein or as disclosed in any of U.S. Pat. Nos. 3,438,737, 4,301,115; 4,637,979. 4,645,842; 4,657,855; 4,704,460; 4,758,508; 3,359,072; 3,418,079. 3,712,853; 3,897,214; 3,802,842; 4,013,416; and 4,385,114; all of which are incorporated by reference herein for this purpose. These reagent test-strips may be employed in the novel method of this invention as further described hereinbelow with the additional requirement being that a measure of eosinophils or other substance characteristic of allergic secretions, such as TAME esterase activity, must be made.

Accordingly, one embodiment of this invention is a simple method for distinguishing patients with allergies and patients with upper respiratory infections involves testing the nasal secretions of these patients with reagent strips disclosed in the aforementioned patents. These dipsticks are inexpensive, and provide an indication of a contacted fluid's pH, protein, glucose, ketone, nitrite, leukocyte esterase, bilirubin and blood content. The patient blows his/her nose on or into a receptacle (for example wax paper or plastic film such as Saran Wrap or the like, or into a collection device specifically adapted for this purpose, as further disclosed herein below), or a swab of nasal secretion is taken, and contacted with the test strip. The pH, protein, nitrite, and leukocyte esterase contents are then evaluated based on the directions of the manufacturer found on the outside of the box in which the commercially available reagent test strips are sold. The procedure generally takes between about sixty seconds to about two minutes. The following table provides results and the meaning thereof:

| | Allergy | Viral Infection | Bacterial Infection (Sinusitis) |
|---|---|---|---|
| pH | 5.0–7.5 | 7.5–9 | 7.5–9 |
| Protein | Trace to + | Trace to + | ++ or +++ |
| Nitrite | Negative* or trace | Negative or trace | ++ or +++ |
| Leukocyte Esterase | Negative* or trace | Trace to + | ++ or +++ |

*Note: "Negative" in this context means a non-positive test result, rather than that a mathematically "negative" score is assigned to this quantity (i.e. no detectable presence of the item being measured).

mathematically "negative" score is assigned to this quantity (i.e. no detectable presence of the item being measured).

This data can be visualized by referring to FIG. 1 which provides a graphic representation of the different chemical read-outs obtained by contacting reagent test strips with the nasal secretions of multiple patients presenting with respiratory discomfort. Closed circles (●) represent patients with radiologically proven sinusitis; open circles (○) represent patients having no sinusitis based on radiological investigation; open squares (□) represent patients with radiologically proven sinusitis that were at least partially treated with antibiotics prior to or during the evaluation period. As can be seen from FIG. 1, there is a clustering in the data points for the pH, protein, nitrite and leukocyte esterase contents of patients with or without sinusitis.

Figure 2:
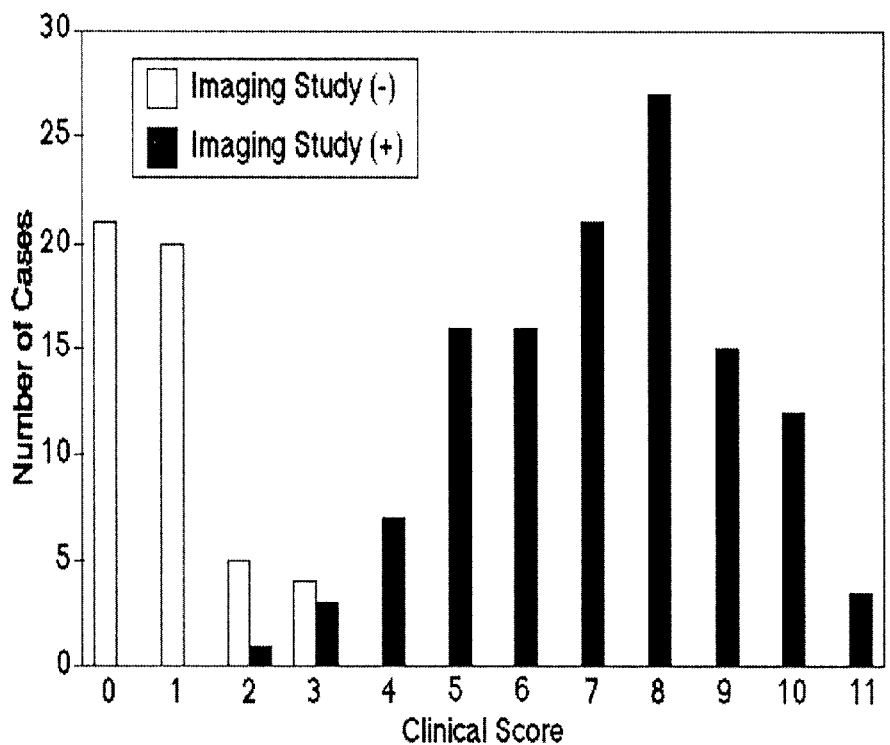
FIG. 2 is a histogram based on the data shown in FIG. 1. From the raw data of FIG. 1, a point system was established such that; pHs greater than or equal to 8.5 received a score of +3, a pH between 8.0 and 8.4 received a score of +2, a pH between 7.25 and 7.9 received a score of +1 and a pH between 5.0 and 7.25 received a score of zero; protein content between about 30–100 mg/dl was given a score of +1; between about 100 mg/dl and 300 mg/dl was given a score of +2; protein between about 300 mg/dl and 2000 mg/dl was given a score of +3; and protein greater than 2000 mg/dl received a score of +4; low nitrite concentrations received a score of +1; moderate amounts of nitrite received a score of +2 and high amounts of nitrite received a score of +3; leukocyte esterase activity in small amounts received a score of about +1, a score of +2 was assigned moderate amounts and a score of +3 was assigned to large amounts of leukocyte esterase. By summing the scores assigned to pH, nitrite, protein, and leukocyte esterase, the histogram of FIG. 2 was produced. Patients radiologically confirmed to have sinusitis are shown with dark bars; patients radiologically clear of sinusitis are shown by open bars.

To aid in the differential diagnosis of allergic rhinitis, viral URI and sinusitis, we have discovered that by assigning a point system to several parameters measured from the mucus secretions of the patients, delimited differential scattering of the patient populations can be achieved with only a minor amount of overlap between patients having these various clinical conditions. FIG. 2 is a histogram based on the data shown in FIG. 1. From the raw data of FIG. 1, a point system was established such that; pHs greater than or equal to 8.5 received a score of +3, a pH between 8.0 and 8.4 received a score of +2, a pH between 7.25 and 7.90 received a score of +1 and a pH between 5.0 and 7.25 received a score of zero; protein content between about 30–100 mg/dl was given a score of +1; between about 100 mg/dl and 300 mg/dl was given a score of +2; protein between about 300 mg/dl and 2000 mg/dl was given a score of +3 and protein greater than 2000 mg/dl received a score of +4; low nitrite concentrations received a score of +1; moderate nitrite concentrations received a score of +2; high concentrations of nitrite received a score of +3; leukocyte esterase activity in small amounts received a score of about +1, a score of +2 was assigned to moderate amounts and a score of +3 was assigned to large amounts of leukocyte esterase. By summing the scores of the pH, nitrite, protein, and leukocyte esterase, the histogram of FIG. 2 was produced. Patients radiologically confirmed to have sinusitis are shown with dark bars; patients radiologically clear of sinusitis are shown by open bars. This method of differential diagnosis can be used with any method of collecting the pH, protein, leukocyte esterase, and nitrite, and is not restricted to the use of reagent indicator strips. The use of reagent indicator strips is, however, one of the most easily conducted, inexpensive and rapid methods for achieving this analysis.

The level of eosinophil infiltration is easily estimated in one embodiment of the invention using high power field microscopy (about 400×magnification) by determining the percentage of total cells that are eosinophils in a Hansel's stained smear of nasal secretion.

According to the package insert of the AMES 9SG Multistix® product, the following information, supplied for urinalysis by that manufacturer, may be directly applied to the novel utility disclosed and claimed herein, and is hereby in corporated as follows:

REAGENT STRIPS for mucus analysis are firm plastic strips to which are affixed several separate reagent areas. Depending on the product being used, AMES REAGENT STRIPS provide tests for glucose, bilirubin, ketone (acetoacetic acid), specific gravity, blood, pH, protein, urobilinogen, nitrite, and leukocytes in urine. A user of these strips refers to the carton and bottle label for specific reagent areas on the product being used.

The reagent test areas on AMES REAGENT STRIPS are ready to use upon removal from the bottle and the entire reagent strip is disposable. The strips may be read visually, requiring no additional laboratory equipment for testing. Certain configurations of strips may also be read instrumentally, using the CLINITEK® family of Urine Chemistry Analyzers and the appropriate Program Module or Program Card from AMES.

The directions must be followed exactly. Accurate timing is essential to provide optimal results. The reagent strips must be kept in the bottle with the cap tightly closed to maintain reagent reactivity. We have surprisingly found that in six samples tested immediately after collection of nasal secretions or six hours after collection and refrigeration, identical results were obtained. Through this finding, those skilled in the art may conclude that the method disclosed herein may be practiced immediately after collection of nasal secretions, or may be stored for later measurement.

Chemical Principles of the Procedure pH: This test is based on a double indicator principle that gives a broad range of colors covering the entire urinary pH range. Colors range from orange through yellow and green to blue.

Protein: This test is based on the protein-error-of-indicators principle. At a constant pH, the development of any green color is due to the presence of protein. Colors range from yellow for "Negative" through yellow-green and green to green-blue for "Positive" reactions.

Nitrite: At the acid pH of the reagent area, nitrite in the nasal secretion reacts with p-arsanilic acid to form a diazonium compound. This diazonium compound in turn couples with 1,2,3,4-tetrahydrobenzo(h)quinolin-3-ol to produce a pink color. The intensity of the pink color developed is used as the basis for assigning the nitrite concentration score as described above.

Leukocytes: Granulocytic leukocytes contain esterases that catalyze the hydrolysis of the derivatized pyrrole amino acid ester to liberate 3-hydroxy-5-phenyl pyrrole. This pyrrole then reacts with a diazonium salt to produce a purple product. The intensity of the purple color developed is used to assign a value to esterase activity as described above.

TAME esterase: As noted above, Eggelston et al., and Baumgarten et al., have noted that TAME-esterase is not elevated during influenza A or rhinoviral infections, while in allergic rhinitis, there is esterase elevation. Accordingly, in one embodiment of the present invention, a chromogenic substrate, such as Tosyl-Arg-paranitrophenol ester or paranitroaniline, Z-Arg-paranitroaniline (Bachem, Cat. #L1220), a derivative of Tosyl-Arg-paranitro phenol ester designed to liberate 3-hydroxy-5-phenyl pyrrole, which may then be reacted with a diazonium salt, or like colorimetric reagents are included as diagnostic discriminators for allergic rhinitis. Development of color on contact of this reagent with nasal secretion therefore would be indicative of allergic rhinitis.

REAGENTS (Based on Dry Weight at Time of Impregnation)

pH: 0.2% w/w methyl red; 2.8% w/w methyl red; 2.8% w/w bromthymol blue; 97.0% w/w non-reactive ingredients.

Protein: 0.3% w/w tetrabromphenol blue; 97.3% w/w buffer; 2.4% w/w nonreactive ingredients.

Nitrite: 1.4% w/w p-arsanilic acid; 1.3% w/w 1,2,3,4-tetrahydrobenzo-(h)-quinolin-3-ol; 10.8% w/w buffer; 86.5% w/w nonreactive ingredients.

Leukocytes: 0.4% w/w derivatized pyrrole amino acid ester; 0.2% w/w diazonium salt; 40.9% w/w buffer; 58.5% w/w nonreactive ingredients.

Those skilled in the art will recognize that other chemical components may be used for carrying out the method disclosed herein.

Recommended Procedures for Handling Reagent Strips: All unused strips must remain in the original bottle. Transfer to any other container may cause reagent strips to deteriorate and become unreactive. Do not remove desiccant(s) from bottle. Do not remove strip from the bottle until immediately before it is to be used for testing. Replace cap immediately and tightly after removing reagent strip. Do not touch test areas of the reagent strip. Work areas and specimen containers should be free of detergents and other contaminating substances.

Dip test areas in mucus completely, but briefly, to avoid dissolving out the reagents. If using strips visually, read test results carefully at the times specified, in a good light (such as fluorescent) and with the test area held near the appropriate Color Chart on the bottle label. Do not read the strips in direct sunlight. If the strips are used instrumentally, carefully follow the directions given in the appropriate instrument operating manual. Protection against ambient moisture, light and heat is essential to guard against altered reagent.

Discoloration or darkening of reagent areas may indicate deterioration. If this is evident, or if test results are questionable or inconsistent with expected finding, the following steps are recommended: (1) confirm that the product is within the expiration date shown on the label; (2) check performance against known positive control materials (e.g., CHEK-STIX® Control Strips); (3) retest with fresh product.

The following procedure should be followed exactly to achieve reliable test results:

1. Collect fresh mucus specimen on a non-absorbent surface.
2. Remove one strip from the bottle and replace cap. Completely immerse reagent areas of the strip in fresh mucus and remove immediately to avoid dissolving out reagents.
3. If reading visually, compare reagent areas to corresponding Color Chart on the bottle label at the time specified. Hold strip close to color blocks and match carefully. Avoid laying the strip directly on the Color Chart, as this will result in soiling the chart.
4. If reading instrumentally, carefully follow the directions given in the appropriate instrument operating manual.

Proper read time is critical for optimal results. If using strips visually, read the pH, protein, and nitrite at 60 seconds; and leukocytes at 2 minutes. The pH and protein areas may also be read immediately or at any time up to 2 minutes after dipping.

After dipping the strip, check the pH area. If the color on the pad is not uniform, read the reagent area immediately, comparing the darkest color to the appropriate Color Chart. All reagent areas except leukocytes may be read at about 1 minute for identifying negative specimens and for determination of the pH. A positive reaction (small or greater) at less than 2 minutes on the leukocyte test may be regarded a positive indication of leukocytes. Color changes that occur after 2 minutes are of no diagnostic value. If using strips instrumentally, the instrument will automatically read each reagent area at a specified time.

For best results, performance of reagent strips should be confirmed by testing known negative and positive specimens or controls whenever a new bottle is first opened. Negative and positive specimens or controls may also be randomly hidden in each batch of specimens tested. Each laboratory should establish its own goals for adequate standards of performance, and should question handling and testing procedures if these standards are not met. CHEK-STIX® Urinalysis Control Strips (#1360) from AMES®, with positive or defined results, provide a convenient basis for quality control program.

Results with AMES REAGENT STRIPS are obtained in clinically meaningful units directly from the Color Chart comparison when using strips visually. With instrumental use, the reagent pads are "read" by the instrument and the results are displayed or printed.

The color blocks and instrumental display values represent nominal values; actual values will vary around the nominal values.

pH: If proper procedure is not followed and excess mucus remains on the strip, a S phenomenon known as "runover" may occur, in which the acid buffer from the protein reagent will run onto the pH area, causing a false lowering of the pH result.

Protein: Contamination of the nasal secretion specimen with quaternary ammonium compounds (e.g., from some antiseptics and detergents) or with skin cleansers containing chlorhexidine may also produce false positive results.

Nitrite: Pink spots or pink edges should not be interpreted as a positive result. Any degree of uniform pink color development should be interpreted as a positive nitrite test.

Leukocytes: Elevated glucose concentrations ($\geq 3$ g/dl) or high specific gravity may cause decreased test results. The presence of cephalexin (Keflex®), cephalothin (Keflin®), or high concentrations of oxalic acid may also cause decreased test results. Tetracycline may cause decreased reactivity, and high levels of the drug may cause a false negative reaction.

Leukocytes: Normal nasal secretion will generally yield negative results; positive results (small or greater) are clinically significant. Individually observed trace results may be of questionable clinical significance; however, trace results observed repeatedly may be clinically significant. Positive and repeated trace results indicate the need for further testing of the patient and/or nasal specimen, according to medically accepted procedures.

Specific Performance Characteristics: Specific performance characteristics are based on clinical and analytical studies. In clinical specimens, the sensitivity depends upon several factors: the variability of color perception; the presence or absence of inhibitory factors, the specific gravity, and the pH; and the lighting conditions when the product is read visually. Because the color of each reagent area changes as the analyte concentration increases, the percentage of specimens detected as positive will increase with the analyte concentration.

Each color block or instrumental display value represents a range of values. Because of specimen and reading variability, specimens with analyte concentrations that fall between nominal levels may give results at either level. Exact agreement between visual results and instrumental results might not be found because of the inherent differences between the perception of the human eye and the optical system of the instruments.

pH: The pH test area measure pH values generally to within 1 unit in the range of 5–8.5 visually and 5–9 instrumentally.

Protein: The reagent area is m ore sensitive to albumin than to globulins, hemoglobin, Bence-Jones Protein and mucoprotein; a negative result does not rule out the presence of these other proteins.

Nitrite: Comparison of the reacted reagent area against a white background may aid in the detection of low levels of nitrite ion, which may otherwise be missed.

Availability: AMES REAGENT STRIPS for Urinalysis are available in bottles of 100 strips: MULTISTIX® 10 SG (#2300A); MULTISTIX® 9 (#2301A); MULTISTIX® 9 SG (#2303A); MULTISTIX® 8 SG (#2304A); MULTISTIX® 7 (#2305A); N-MULTISTIX® SG (#2740A); MULTISTIX® SG (#2741A); N-MULTISTIX® (2829A); MULTISTIX® (#2820A); and BILI-LABSTIX® (#2814A).

Any of these or other commercially available reagent test strips which provide pH, protein, nitrite, leukocyte esterase and preferably also eosinophil and/or TAME esterase activity data can be used according to this disclosure to differentiate between bacterial infections, viral infections and allergic conditions. Thus, in a fashion completely analogous to that described above for the Ames REAGENT STRIPS, commercially available reagent test strips produced by Boehhringer Mannheim Corporation may be use d or adapted for this purpose. For example CHEMSTRIP 9, Catalog No. 417109, provides a readout for leukocytes, nitrite, pH, protein and several other analytes. The information provided in the package insert for the CHEMSTRIP 6, 7, 8, 9, 10 (which also provides a readout for specific gravity), is largely analogous to the information provided hereinabove from the Multistix® product. In our hands, testing of nasal secretions using the Boelringer product yielded results which, according to this invention, are similar to those obtained using the Multistix® product. Slight adjustments in the color readouts and values thereof may be needed due to the differences between the color charts used by the two manufacturers, but, based on the instant disclosure, those skilled in the art are able to make any necessary adjustments.

In one aspect of the invention, there is provided a reagent test strip specifically adapted for rapidly, non-invasively and inexpensively differentiating between allergic conditions and respiratory, viral and bacterial infections. In use, the test strip is optimized to provide information about nasal mucus secretions including, but not limited to, the pH, protein content, nitrite, leukocyte esterase activity and level of eosinophil infiltration, such that all of the information presented in FIG. 2 and a separate indication of the presence or absence of allergy can be obtained from a single indicator strip. This is achieved, for example, by preparing a reagent test strip according to commercially available strips, but in addition, providing a means for measuring the amount of eosinophil cationic protein (ECP) or another eosinophil specific protein or enzyme present in the nasal secretion, the presence of which is proportional to the amount of eosinophil infiltration. Alternatively, the test strip could be made so as to selectively trap eosinophils, and the assay could then be for any substance found in eosinophils (such as an enzyme or any other detectable substance), without it being necessary for the substance to be specific for eosinophils. The novel reagent test strip of this invention, therefore, can include an indicator location on the strip comprising immobilized eosinophil cationic protein (ECP) or other appropriate protein bound to labeled anti-ECP antibody or other specific antibody. In this event, the strip is contacted with mucus from a patient and all of the other parameters, (pH, protein, nitrite, leukocyte esterase) are read from the strip. The strip is then incubated for a sufficient amount of time so that ECP present in the mucus, due to eosinophil infiltration, competes the labeled antibody from the strip-bound ECP. As a result, upon visualization of the label, the greater the amount of ECP present in the mucus, the lower the amount of label visualized. The antibody could be enzymatically labeled, or labeled with biotin or avidin, which could then be visualized by methods well known in the art. Analogously, ECP or other eosinophil antigen specific antibody could be immobilized on the strip which, upon exposure to nasal secretions, binds any ECP or other eosinophil specific protein or enzyme present in the secretion. Excess sample could then be washed from the strip and a second, labeled ECP or other eosinophil antigen specific antibody or chromogenic eosinophil specific enzyme substrate could be contacted with the strip. In this case, the greater the signal upon development, the greater the amount of eosinophilia in the patient.

Preferably, an eosinophil specific enzyme is detected by providing a chromogenic reagent on the strip which changes color to an extent proportional to the amount of eosinophils present in the sample. In this context, the teachings of U.S. Pat. Nos. 5,369,007 and 5,200,321, herein incorporated by reference, while directed to a very different art (detection of illicit drugs) are instructive here. According to those patents, a microassay on a card could be adapted to the instant utility in either a displacement or competition mode, as described herein above, using eosinophil specific antigens and antibodies. Likewise, the concepts and methods disclosed therein could be utilized to prepare the novel reagent test strip of the instant invention. In yet another embodiment of the novel test strip of this invention, a portion of the strip contacted with the nasal secretion is transparent. This portion is then simply stained and quantitated microscopically for eosinophils as described hereinabove, after reading all of the other reagent parameters. In addition, measuring the level of TAME esterase activity in the secretion provides a further indication of whether an allergic condition is present in a given patient.

In any event, even with the use of a standard, commercially available reagent test strip, all that is required for the method of this invention is that, in addition to contacting the nasal secretion with an appropriate reagent test strip and quantitation of the pH, nitrite, leukocyte esterase and protein, is that the mucus be evaluated for eosinophils. This is quickly and easily achieved by making a smear of the nasal secretion, staining the smear with eosine or other appropriate dye, and quantitating the number of eosinophils present per field. Alternatively, the hemocytometric method of Okuda et al. (Int Arch Allergy Immunol. [1994] 104:6) or of Settipane (Allergy Proc. [1985] 6:303–366), herein incorporated by reference, could be used for this purpose.

According to methods known in the art, nasal ECP has been found to range between about 30 ng/ml in a "normal" individual, up to about 200 ng/ml in individuals experiencing acute allergic reactions (see Clin. Exp. Allergy, 1997, 27:270–276; see also JACI 1996, 97:104–112; see also Clin. Exp. Allergy 1994, 24:1151–1156). Commercially available antibodies for carrying out the method and for making the device according to the present invention may be obtained, for example, from Pharmingen. Thus, Pharmingen catalog number 15371A is a mouse IgG1 monoclonal antibody (clone AHE-1) which recognizes human eosinophil peroxidase, an 81 kD granule protein specific to eosinophils. Pharmingen catalog number 15381A is a mouse IgG1 monoclonal antibody (clone AHE-2) which recognizes human eosinophil Major Basic Protein, a 14 kD granule protein specific to eosinophils. Accordingly, a wide variety of eosinophil specific markers may be employed according to the method and for the device of this invention. Thus, a protein selected from the group, but not limited to the group, eosinophil major basic protein (MBP), present at about 9 μg/million eosinophils, eosinophil cationic protein (ECP), present at about 5 μg/million eosinophils, eosinophil derived neurotoxin (EDN), present at about 3 μg/million eosinophils, or eosinophil peroxidase (EPO), present at about 12 μg/million eosinophils, (see Textbook of Allergy, Principles and Practice, for concentrations of these markers), may be employed in the device or method according to this invention, using commercially available antibody, or antibody developed independently. As mentioned above, avidin/biotin conjugates of such eosinophil specific markers may also be employed according to this invention.

Accordingly, this invention provides a method for rapidly, non-invasively and inexpensively differentiating between allergy and viral or bacterial respiratory infection. The method involves measuring the pH, protein content, nitrite content, leukocyte esterase activity and eosinophil content or other substance found in the secretions of allergic individuals, such as TAME esterase, of a sample of contacted nasal secretion. A combination of a pH between about 7.5 and 9, a moderately strong presence of protein, and at least a trace of nitrite and leukocyte esterase as quantitated by the scoring method of FIG. 2 indicates the presence of a bacterial infection. The combination of a pH between about 5.0 and 7.0, little or no protein, little or no nitrite, little or no leukocyte esterase activity (i.e. a low score on the scoring system) and moderate to strong eosinophil content or TAME esterase activity is indicative of an allergic condition. The combination of a pH between about 5 and 7, little or no protein, nitrite or leukocyte esterase and the absence of eosinophil infiltration indicates an upper respiratory tract viral infection. In a preferred embodiment of this method, each value obtained for pH, protein, nitrite, leukocyte esterase in a patient's nasal secretion is assigned a value such that the sum of assigned values results in an enhancement in the clustering of patient data having bacterial sinusitis infections. A separate set of values is established to determine the presence or absence of allergic rhinitis, based on eosinophils, their surrogate markers and/or other substances in nasal secretions of patients suffering from allergic rhinitis, such as TAME esterase. This is not to say the measurement has to be conducted separately. Actually, the TAME esterase analysis or eosinophil concentration analysis or both may be conducted at the same time as the measurement of other parameters, either by using an appropriate dip-stick, collection device as disclosed herein, or by using pads of reagents sensitive to each test substance. However, the measurement of eosinophils or TAME esterase are not summed with the remaining measurements. Those measurements are summed separately according to the method of this invention, and the eosinophil or TAME esterase measurement is interpreted independently of the other test results.

In a preferred embodiment, this method is practiced with a reagent test strip. The test strips which are used in this testing may be those produced by the Ames division of Miles is laboratory as disclosed in any of U.S. Pat. Nos. 3,438,737;

4,301,115; 4,637,979; 4,645,842; 4,657,855; 4,704,460; 4,758,508, or by Boehringer Mannheim Corporation, as disclosed in any of U.S. Pat. Nos. 3,359,072; 3,418,079; 3,712,853; 3,897,214; 3,802,842; 4,013,416; 4,385,114. A reagent test strip specifically adapted for rapidly, non-invasively and inexpensively differentiating between allergy and respiratory infection is also provided. This novel strip comprises reagents adapted to provide information on the pH, protein content, nitrite content, leukocyte esterase activity and eosinophil content or TAME esterase activity of the sample contacted. Absence of sinusitis and allergic rhinitis in the presence of rhinorhea indicates the presence of a viral infection.

Figure 3:
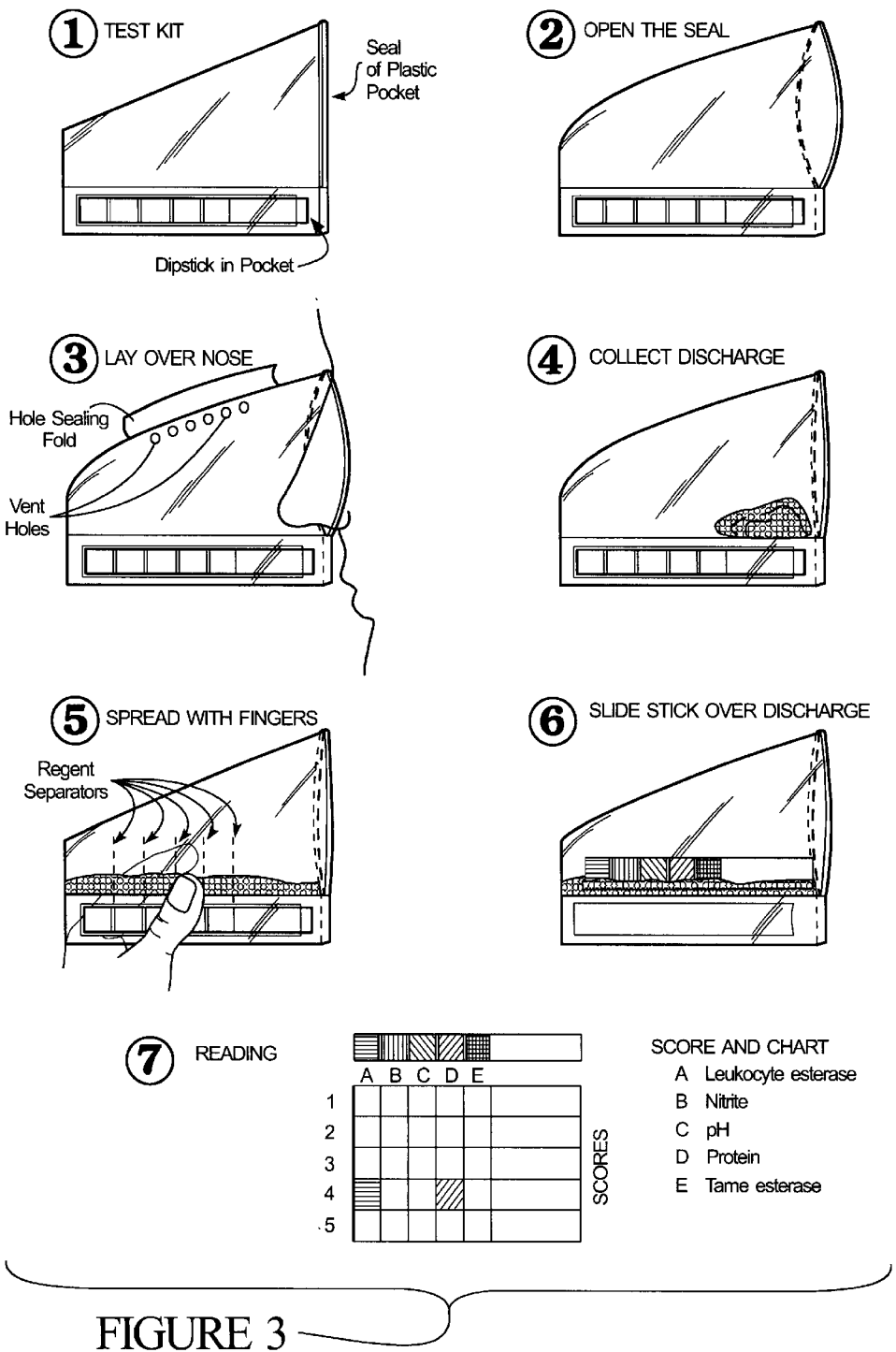
FIG. 3 provides a graphic representation of the novel test kit and collection apparatus of this device, as well as an illustration of the method of use thereof.

In a further aspect of the present invention, as disclosed with reference to FIG. 3, there is provided a novel collection device for home or point of use care for the collection of nasal secretions and for conducting diagnosis therewith, without the need for end-user contact with nasal secretion samples. In one embodiment, the collection apparatus is a bag into which a patient blows their nose. In order to prevent the bag from bursting, in one embodiment, the bag comprises a series of air vents located so as to permit air blown into the bag to escape, without at the same time permitting nasal secretions to escape from the container. This is most conveniently accomplished by designing the collection device to fit snugly about the nose of a patient, such that upon blowing nasal secretions into the bag, the secretions are deposited onto a bottom aspect of the bag, while air blown into the bag is permitted to escape from a series of holes disposed at a top aspect of the bag. This element of the invention is shown in FIG. 3, panel (1). Once the nasal secretion is deposited within the collection device, it may be desirable to seal the holes, if present. This is accomplished by provision of a piece of tape for this purpose. Alternative means for sealing the holes include provision of a flap element which may be folded over the holes, thereby sealing the holes; provision of a cardboard, plastic or like sealing means, and equivalents thereof which would be suggested to those of ordinary skill in the art, based on the present disclosure. Thus, for example, in certain embodiments of this invention, a pre-crimped patient label is folded over with an adhesive strip to ensure that none of the nasal secretion oozes out of the sample container during handling. Naturally, the patient label and sealing means may also be provided as separate elements. Thus, a patient label may be affixed to the collection device, or the collection device may be manufactured with a segment adapted to receive indelible patient identification markings.

In addition, this embodiment of the invention shows a marginal aspect of the collection device as a sealable edge, such that after the nasal secretions have been blown into the collection device, the nasal secretions may be isolated from contact with external surfaces. The seal may be created by any of a number of means known in the art, such as by means of a "zip-lock" means, wherein a first edge of the sealable margin comprises a strip of material which fits into a groove on the second edge of the sealable margin, thereby sealing the contents within the collection device. Alternatively, a fold-over sealing flap may seal the marginal edge of the collection device through which the patient inserts their nose to deposit nasal secretions. The fold-over flap may itself have a pressure-sensitive adhesive strip disposed thereon, such that upon folding the flap over the edge into which the nose is placed and then removed, after deposit of nasal secretion, the flap may be made to seal on an external surface adjacent the opening. Alternate means for sealing the collection device may be employed without departing from the substance of this invention. Such modifications, equivalents or variations of the sealing means as would be suggested to one of ordinary skill in the art, based on the present disclosure, are therefore incorporated herein.

Accordingly, with reference to FIG. 3, in one aspect of this invention, a bag-like collection device is provided which may be sealingly opened. The collection device is positioned over the nose of a patient and the nasal discharge is collected. Where an integral indicator device is included in the apparatus, the nasal secretion may be spread over the indicator device by external application of a spreading pressure. Appropriate time intervals are then observed, as disclosed herein, prior to reading the test results. In the event that nasal secretions are being collected from a child or infant, it will be appreciated that it may be necessary to wipe or squeeze nasal secretion from the nasal passage of the infant or child.

It should be appreciated by those skilled in the art that the embodiment of this invention shown in FIG. 3 is merely suggestive, and that the collection device need not be limited to the specifics as shown therein. Thus, the indicator device may be contained in a separate container and inserted into the collection device, prior, concurrent with or subsequent to collection of the nasal secretion. The nasal secretion, once collected and coded for a particular patient, may also be stored, either at ambient temperature, or in a cooled environment, until such time as the sample may be analyzed. At that time, the indicator device may be brought into contact with the nasal secretion to provide the differential readout as disclosed herein.

It will further be appreciated that the configuration of the collection device may be subject to various modifications, as defined by such practical considerations as the desire to avoid patient embarrassment. One element that may assist in this regard is to provide a colored or opaque collection device. In this embodiment, the indicator device may need to be withdrawn from the collection device to permit accurate reading of the test results. Alternatively, the colored or opaque element may be affixed to the collection device in a detachable format such that the coloration or opaque coating may be removed when the indicator device is to be read.

In a further embodiment of this invention, the collection device may be configured so as to minimize the possibility of reagent cross contamination. For example, where a pH reagent is directly adjacent a protein responsive reagent, it might be the case that buffer leaching from the pH sensitive reagent might negatively impact on the protein concentration reading, or vice versa. In order to minimize this possibility, a series of vertical separations may be defined between adjacent pads of reactive reagents. In this manner, each reagent may be individually contacted with nasal secretion, without the danger of cross contamination of one reagent with another.

In yet a further embodiment of this invention, the reactive reagents, whether directly applied to a surface of the collection device or placed in the collection device in the form of a reagent strip, it may be beneficial for the reactive reagents to be physically separated by a separation means until such time as the analysis is to be conducted. If the analysis is to be conducted right away, upon collection of nasal secretion, the barrier may be removed or perforated, so that nasal secretion may contact the reagent pads. If the analysis is to be conducted some time after collection of the nasal secretion, the barrier means may be left intact, and removed only when the analysis is to be conducted. Alternative means for creating such a barrier include the possibility of including a fold in the collection device, a zip-lock feature, a breakable barrier or the like, separating the main chamber of the collection device from the reactive reagents.

It will also be appreciated that in order to facilitate manufacture or distribution, the collection device may be formed on a continuous roll or the like. In this manner, multiple collection devices may be releasably attached to each other. When the need arises for a differential diagnosis to be made, one collection element is disconnected from the remaining collection devices and is used individually. It will further be appreciated that the indicator elements may be combined into a single indicator element, and such indicator element may comprise an electronic means for data collection or analysis.

It will further be suggested to those skilled in the art, based on the present disclosure, that a kit may be provided for conducting nasal secretion analyses. Such a kit might include a sample collection device, such as the nasal secretion collection bag shown in FIG. 3. The kit might further include either an integral means for providing the differential diagnostic readout disclosed herein, or a separate means for providing the differential diagnostic readout. Thus, a dipstick might be included in the kit as a separate element, the dipstick may be included within the collection apparatus, or different chemicals as defined herein may be affixed directly on an aspect of the collection apparatus with which the collected nasal secretions may be brought in contact. Furthermore, it will be appreciated that the shape or configuration of the collection apparatus may be varied, without departing from the scope of this invention. Thus, round, square, elliptical or like shapes for the collection apparatus may be contemplated, in addition to the essentially trapezoidal shape of the device exemplified in FIG. 3.

Having generally described the present invention, including the best mode for practicing the invention, reference is now made to the attached claims, which define the scope of exclusivity claimed herein.

REFERENCES

Service, R. F. (1995) *Science* 270:724–727.

Katz, et al. (1995) *Allergy Proc.* 16:123–127.

Wang, et al. (1995) "Correlations between Complaints, Inflammatory Cells and Mediator Concentrations in Nasal Secretions after Nasal Allergen Challenge and during Natural Allergen Exposure," *Int. Arch. Allergy Immunology* 106:278–285.

Sigurs, et al. (1994) "Eosinophil cationic protein in nasal secretion and in serum and myeloperoxidase in serum in respiratory syncytial virus bronchiolitis: relation to asthma and atopy," *Acta Paediatr* 83:1151–1155.

Okuda, et al. (1994) "A Novel Method of Counting Eosinophils in Nasal Secretion of Allergic Rhinitis by Hemocytometric Method," *Int. Arch. Allergy Immunol.* 104 (suppl. 1):6.

Kowalski, et al. (1993) "Neutrophil chemotactic activity (NCA) in nasal secretions from atopic and nonatopic subjects," *Allergy* 48:409–414.

Igarashi, et al (1993) "Analysis of nasal secretions during experimental rhinovirus upper respiratory infections," *J. Allergy Clin. Immunol.* 92:722–731.

Sperber, et al. (1993) "In vivo detection of a novel macrophage-derived protein involved in the regulation of nasal mucus-like glycoconjugate secretion," *J. Allergy Clin. Immunol.* 92:581–588.

Knani, et al. (1992) "Indirect evidence of nasal inflammation assessed by titration of inflammatory mediators and enumeration of cells in nasal secretions of patients with chronic rhinitis," *J. Allergy Clin. Immunol.* 90:880–889.

Klementsson, et al. (1991) "Eosinophils, secretory responsiveness and glucocorticoid-induced effects on the nasal mucosa during a weak pollen season," *Clinical and Experimental Allergy* 21:705–710.

Gordon, et al. (1991) "The pathophysiology of rhinitis," *J. Allergy Clin. Immunol.* 88:33–42.

Cohen, R. A, E. P. Brestel (1988) "Nasal secretory response to allergen provocation, " *Clinical Allergy* 18:435–443.

Liu, et al. (1988) "Injurious effect of eosinophil extract on the human nasal mucosa," *Rhinology* 26:121–132.

Anderson, et al. (1987) "Allergen-induced nasal hyperactivity appears unrelated to the size of the nasal and dermal immediate allergic reaction," *Allergy* 42:631–637.

Settipane, G. A, D. E. Klein (1985) "Non Allergic Rhinitis: Demography of Eosinophils in Nasal Smear, Blood Total Eosinophil Counts and IgE Levels," *NER Allergy Proc.* 6:363–366.

Brofeldt, et al. (1986) "Biochemical Analysis of Nasal Secretions induced by Methacholine, Histamine, and Allergen Provocations," *Am. Rev. Respir. Dis.* 133:1138–1142.

Eggelston, et al. (1984) "Mediators of immediate Hypersensitivity in Nasal Secretions during Natural Colds and Rhinovirus Infection," *Acta Otolaryngol.* suppl. 413:25–35.

Baumgarten, et al. (1986) "Plasma Kallikrein During Experimentally Induced Allergic Rhinitis: Role in Kinin Formation and Contribution to TAME-Esterase Activity in Nasal Secretions," *J. Immunol.* 137:977–982.

Anderson, et al. (1995) "Mechanisms of nasal hyperreactivity," Eur. Arch. Otorhinolaryngol 252 (suppl. 1):S22–S26.

Florman, et al. (1987) "Rapid Non-invasive Techniques for Determining Etiology of Bronchitis and Pneumonia in Infants and Children," *Clin. Chest Med.* 8:669–679.

Katz, et al (1995) "A comparison of Imaging Techniques in Patients with Chronic Sinusitis (X-Ray, MRI, A-Mode Ultrasound)," *Allergy Proc.* 16:123–127.

Demoly, et al. (1994) "Assessment of Inflammation in noninfectious chronic maxillary sinusitis," *J. Allergy Clin. Immunol.* 94:95–108.

Atkinson, Roger Lee, Marshall Lloyd Fader, U.S. Pat. No. 3,438,737, issued Apr. 15, 1969.

Rapkin, Myron C., David L. Tabb, U.S. Pat. No. 4,301,115, issued Nov. 17, 1981.

Skjold, A. Christopher, Herbert Hugl, Gerhard Wolfrum, U.S. Pat. No. 4,637,979, issued Jan. 20, 1987.

Corey, Paul F., U.S. Pat. No. 4,645,842, issued Feb. 24, 1987.

Corey, Paul F., Christopher Skjold, James H. Pendergrass, Lonnie Stover, U.S. Pat. No. 4,657,855, issued Apr. 14, 1987.

Corey, Paul F., U.S. Pat. No. 4, 704,460, issued Nov. 3, 1987.

Schnabel, Eugen, James Travis, A. Christopher Skjold, U.S. Pat. No. 4,758,508, issued Jul. 19, 1988.

Kidwell, David A, U.S. Pat. No. 5,369,007, issued Nov. 29, 1994.

U.S. Pat. No. 5,200,321

Rey, Hans-Georg, Peter Rieckmann, U.S. Pat. No. 3,359,072, issued Dec. 19, 1967.

Rey, Hans-Georg, Peter Rieckmann, U.S. Pat. No. 3,418,079, issued Dec. 24, 1968.

Rittersdorf, Walter, Hans-Georg Rey, Peter Rieckmann, U.S. Pat. No. 3, 712,853, issued Jan. 23, 1973.

Lange, Hans, Walter Rittersdorf, Hans-Georg Rey, U.S. Pat No. 3,897,214, issued Jul. 29, 1975.

Lange, Hans, Walter Rittersdorf, Hans-Georg Rey, Peter Rieckmann, U.S. Pat. No. 3,802,842, issued Apr. 9, 1974.

Rittersdorf, Walter, Werner Güthlein, Wolfgang Werner, Hans-Georg Rey, Peter Rieckmann, U.S. Pat. No. 4,013,416, issued Mar. 22, 1977.

Güthlein, Werner, Walter Rittersdorf, Hugo Tiedemann, Peter Vogel, Wolfgang Werner, U.S. Pat No. 4,385,114, issued May 24, 1983.

What is claimed is:

1. A method for differentiating between allergic rhinitis, upper respiratory tract viral infection and bacterial sinusitis, which comprises measuring a sample of a patient's nasal secretion for pH, protein concentration, nitrite concentration, leukocyte esterase activity, and eosinophil counts or TAME esterase activity or both, such that a scoring system is developed through a combination of:
   (a) a pH between about 7.5 and 9, a moderately strong presence of protein, nitrite or leukocyte esterase, and low or absent eosinophil counts or TAME esterase activity is indicative of bacterial sinusitis without an allergic condition;
   (b) a pH between about 5 and 7, little or no protein, little or no nitrite, little or no leukocyte esterase activity, and moderate to significant TAME esterase activity or moderate to high eosinophil counts is indicative of allergic rhinitis; and
   (c) a pH between about 5 and 7, little or no protein, low concentration or a trace of nitrite or a trace of leukocyte esterase or both and low or absent eosinophil counts or low or absent TAME esterase activity indicates an upper respiratory tract viral infection; wherein said method comprises deposition by a patient of a nasal secretion sample within a collection apparatus adapted for receipt of said sample for concurrent or subsequent contact with reagents indicative of the pH, protein, nitrite, leukocyte esterase, eosinophil or TAME esterase concentrations.

2. The method of claim 1 wherein said collection apparatus comprises a sealable container for said nasal secretion sample.

3. The method of claim 2 wherein said container further comprises a unitary reagent test strip.

4. The method of claim 2 wherein a reagent test strip is inserted into said container to obtain a differential diagnostic readout.

5. The method according to claim 4 wherein said container comprises a series of holes disposed so as to permit air blown into said container to escape, without at the same time permitting said nasal secretion to escape.

6. The method according to claim 5 wherein said container comprises a means for sealing said series of holes to prevent nasal secretion from oozing from said container.

7. The method according to claim 6 wherein said container comprises a means for associating a particular nasal secretion sample with a particular patient.

8. The method according to claim 1 wherein said pH, protein concentration, nitrite concentration, and leukocyte esterase activities are each assigned a score, such that upon analysis of summed scores for these measures, a clear clustering of patient data measurements occurs such that summed data from patients suffering from allergic rhinitis is substantially separated from patient data from patients afflicted with viral respiratory infection and wherein data from such patients is substantially separated from patients afflicted with sinusitis.

\* \* \* \* \*